(12) United States Patent
Kaeppeli

(10) Patent No.: US 10,288,634 B2
(45) Date of Patent: May 14, 2019

(54) DEVICE FOR MOUNTING A PLURALITY OF ACTUATOR MODULES

(71) Applicant: Roche Diagnostics Operations, Inc., Indianapolis, IN (US)

(72) Inventor: Marcel Kaeppeli, Merenschwand (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 34 days.

(21) Appl. No.: 15/435,771

(22) Filed: Feb. 17, 2017

(65) Prior Publication Data

US 2017/0248625 A1 Aug. 31, 2017

(30) Foreign Application Priority Data

Feb. 26, 2016 (EP) .................................... 16157591

(51) Int. Cl.
*B65G 54/02* (2006.01)
*G01N 35/04* (2006.01)
(Continued)

(52) U.S. Cl.
CPC .............. *G01N 35/04* (2013.01); *B65G 54/02* (2013.01); *F16M 1/00* (2013.01); *F16M 13/02* (2013.01);
(Continued)

(58) Field of Classification Search
CPC ... G01N 2035/0401–2035/0415; G01N 35/04; G01N 2035/0418;
(Continued)

(56) References Cited

U.S. PATENT DOCUMENTS 2,751,817 A * 6/1956 Lapekas ................ B60R 1/0605
248/282.1
4,123,030 A * 10/1978 Johansson ............... B60R 1/078
248/478
(Continued)

FOREIGN PATENT DOCUMENTS

CN 201827621 U 5/2011
EP 2022736 A1 2/2009
(Continued)

OTHER PUBLICATIONS

Search Report dated Sep. 26, 2016 in Application No. EP 16157591. 5, 8 pages.

*Primary Examiner* — Robert R Raevis
(74) *Attorney, Agent, or Firm* — Roche Diagnostics Operations, Inc.

(57) ABSTRACT

A device for mounting a plurality of actuator modules in a grid pattern to a support frame with support bars is provided. Each actuator module has a regular polygonal basic shape with three, four or six corners. The device comprises a plurality of support brackets mountable to the support bars. Each support bracket is provided with a support structure arranged at a node of the grid pattern and having a cross element adapted to support corner regions of neighboring actuator modules at the node. A transport device comprising a plurality of actuator modules and a device for mounting the plurality of actuator modules in a grid pattern to a support frame is also provided. A laboratory sample distribution system and a laboratory automation system comprising a laboratory sample distribution system are also provided.

6 Claims, 4 Drawing Sheets

(51) Int. Cl.
*F16M 1/00* (2006.01)
*F16M 13/02* (2006.01)
*G01N 35/02* (2006.01)

(52) U.S. Cl.
CPC ... *G01N 35/026* (2013.01); *G01N 2035/0406* (2013.01); *G01N 2035/0477* (2013.01)

(58) Field of Classification Search
CPC ..... G01N 2035/0429; G01N 2035/046; G01N 35/026; G01N 2035/0406; G01N 2035/0477; F16M 1/00; F16M 13/02; F16M 7/00; A47G 29/08; B65G 54/02; A47B 96/07; A47B 96/1425
USPC .............. 248/200–316.8; 73/863.01, 864.23; 422/63, 65, 67; 198/348–371.3, 619, 198/867.04, 863.06
See application file for complete search history.

(56) References Cited

U.S. PATENT DOCUMENTS

| | | | |
|---|---|---|---|
| 9,664,703 B2 | 5/2017 | Heise et al. | |
| 2009/0308994 A1* | 12/2009 | Moore | A22B 5/06 248/229.17 |
| 2014/0234978 A1* | 8/2014 | Heise | B65G 54/02 436/48 |
| 2015/0276776 A1 | 10/2015 | Riether | |
| 2017/0204623 A1* | 7/2017 | Williams | E04F 21/185 |

FOREIGN PATENT DOCUMENTS

| | | | |
|---|---|---|---|
| GB | 2504882 | * | 12/2014 |
| WO | 2013/064656 A1 | | 5/2013 |

* cited by examiner

DEVICE FOR MOUNTING A PLURALITY OF ACTUATOR MODULES

CROSS-REFERENCE TO RELATED APPLICATIONS

This application claims priority to EP 16157591.5, filed Feb. 26, 2016, which is hereby incorporated by reference.

BACKGROUND

The present disclosure relates to a device for mounting a plurality of actuator modules in a grid pattern to a support frame and to a transport device comprising a plurality of actuator modules and a device for mounting the plurality of actuator modules in a grid pattern to a support frame. Further, the invention relates to a laboratory sample distribution system and to a laboratory automation system comprising a laboratory sample distribution system.

A laboratory automation system typically comprises a plurality of pre-analytical, analytical and/or post-analytical stations, in which samples, for example blood, saliva, swab and other specimens taken from the human body, are processed. It is generally known to provide various containers, such as test tubes or vials, containing the samples. The test tubes are also referred to as sample tubes. In the context of the application, containers such as test tubes or vials for containing a sample are referred to as sample containers.

A known laboratory sample distribution system with a transport device comprises a transport plane or driving surface and a plurality of electro-magnetic actuators being stationary arranged below the driving surface and a plurality of sample containers comprising a magnetically active device, preferably at least one permanent magnet. The electromagnetic actuators are adapted to move a sample container carrier placed on top of the driving surface by applying a magnetic force to the sample container carrier. The sample container carriers have a retaining area for retaining sample containers so that sample containers can be placed in an upright or vertical position in the sample container carriers.

However, there is a need for a device for mounting actuator modules of a transport device to a support frame allowing for an easy assembly of the transport device.

SUMMARY

According to the present disclosure, a device for mounting a plurality of actuator modules in a grid pattern to a support frame with support bars is presented. Each actuator module can have a regular polygonal basic shape with three, four or six corners. The device can comprise a plurality of support brackets mountable to the support bars. Each support bracket can be provided with a support structure arranged at a node of the grid pattern and can have a cross element adapted to support corner regions of neighboring actuator modules at node.

Accordingly, it is a feature of the embodiments of the present disclosure to provide for a device for mounting actuator modules of a transport device to a support frame allowing for an easy assembly of the transport device. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
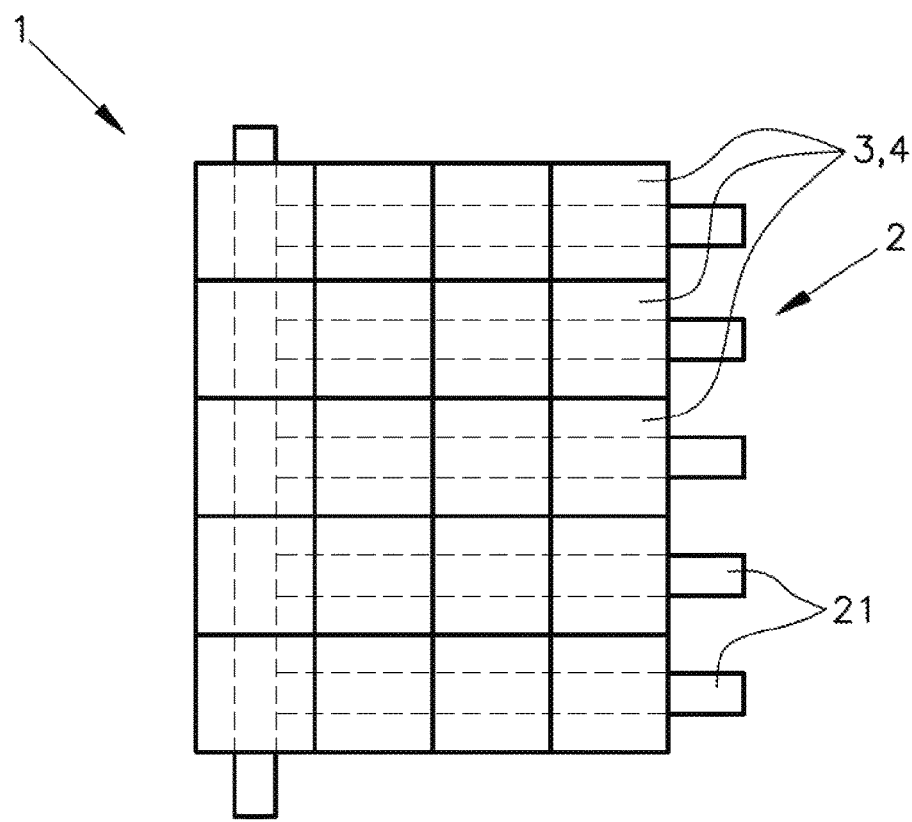
FIG. 1 illustrates a top view of a transport device comprising several actuator modules mounted to a support frame according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A device for mounting a plurality of actuator modules in a grid pattern to a support frame with support bars is provided. Each actuator module can have a regular polygonal basic shape with three, four or six corners. The device can comprise a plurality of support brackets mountable to the support bars. Each support bracket can be provided with a support structure arranged at a node of the grid pattern and can have a cross element adapted to support corner regions of neighboring actuator modules at the node. An actuator module having an at least essentially square basic shape with four corners can be particularly suitable for being supported by four support brackets. Each support bracket can be provided with one support structure arranged at a node of a square grid pattern.

A plurality of support brackets can be mounted to support bars of a support frame in a suitable arrangement. After a framework for a transport device has been built by the plurality of support brackets, the actuator modules can be mounted to the framework.

In one embodiment, the device can comprise fixation elements adapted for fixing the support brackets adjustable in position to the support bars and at least one mounting rail for positioning and aligning at least a subset of the support brackets on one of the support bars of the support frame. For mounting the support brackets to the support bars, suitable fixation elements can be provided such as, for example a slot nut to be inserted into a groove of the support bar. Prior to tightening a respective screw, the slot nut can be moved along the groove for positioning the support bracket along the support bar. The mounting rail can be manufactured with high precision and can allow positioning of a subset of support brackets at the support bars. In one embodiment, the mounting rails can be removed after the support brackets are mounted to the support bars. One mounting rail can be reused for mounting a further subset of support brackets. In other embodiments, the mounting rail can remain on the support frame and/or can be an integral part of the support frame.

The support brackets, in one embodiment, can each be at least substantially L-shaped in a side view comprising a supporting leg with the support structure and mounting leg for mounting the support bracket to the support frame. The L-shape can be advantageous for supporting the actuator module in a position offset in vertical and horizontal direction from the support bar. The L-shaped support brackets can be mounted to the support bar such that the mounting leg can protrude to a side of the support bar in a direction at least substantially perpendicular to the longitudinal axis of the support bar.

The mounting leg can be provided with a throughhole for inserting a fixation screw. In other embodiments of the support brackets, the mounting leg can be provided with a slit for an insertion of a fixation screw perpendicular to a screw axis.

The support bracket, in one embodiment, can be provided with a step in a top view so that the mounting leg can be offset to the supporting leg in a direction substantially perpendicular to a side of the support bracket. In one embodiment, the mounting leg can be offset to the supporting leg over a distance that can equal half the width of the support bracket. The step can allow aligning the support structures of two support brackets by mounting the support brackets to opposite sides of one support bar such that the mounting legs of the two support brackets can abut each other.

For precise positioning of the support structure of the support bracket in a direction substantially perpendicular to the longitudinal direction of the support bar, in one embodiment, the support bracket can be provided with a stop element for limiting a movement of the support bracket towards a support bar of the support frame.

The support structure can comprise a cross element for supporting adjoining corners of neighboring actuator modules. In one embodiment, the cross element can comprise several fingers arranged at angles adapted to an angle of the regular basic shape of the actuator modules so that in each case, one or two fingers can be adapted to support one corner region of one actuator module. In the case that the actuator module has a triangular basic shape, six fingers can be arranged at angles of about 60°. In the case that the actuator module has a square basic shape, four fingers can be arranged at angles of about 90°. In the case the actuator module has a hexagonal basic shape, three fingers can be arranged at angles of about 120°. The fingers, in one embodiment, can be arranged to extend in a direction that can coincide with bisectors of the supported corner regions. Each corner region can be supported by one finger.

In other embodiments, the fingers can be arranged so that in each case two fingers can be adapted to support one corner region of one actuator module. Each finger can be adapted to support the adjacent corner regions of two neighboring actuator modules. In other words, the fingers can extend in parallel to sides of the actuator module adjoining the supported corner region. In one embodiment, the corner regions of the actuator modules can be provided with chamfers allowing arrangement of the actuator module closer to a support structure. Alternatively, or in addition, the support structure can comprise a recess for receiving the corner region.

In one embodiment, the actuator modules can be provided with a planar top surface element serving as a driving surface. In other embodiments, the support structure can be provided with a pillar element adapted to support a driving surface arranged above the actuators. The driving surface can be adapted to carry sample container carriers. In other words, the driving surface and the actuator module can be separate and individually mounted to the support brackets. This can allow, for example, the actuator module to be mounted with less strict tolerances than the driving surface.

The driving surface, in embodiments of the transport device, can be tiled and can comprise a plurality of driving surface modules. Each driving surface module can be detachably mountable to a subset of the support brackets.

To couple the driving surface, or individual driving surface elements, with the support brackets, a top surface of the pillar element, in one embodiment, can be provided with apertures adapted to receive positioning pins provided at a bottom side of a driving surface panel covering at least a subset of actuator modules or at a bottom side of driving surface modules.

At least some of the support brackets, in one embodiment, can be provided with a cable support, in order to position and support cables and/or other media supply lines for a media supply of the transport device.

A transport device for a laboratory sample distribution system with a plurality of actuator modules, each actuator module comprising a plurality of electro-magnetic actuators, and with a device for mounting the plurality of actuator modules in a grid pattern to a support frame can be provided.

A laboratory sample distribution system can be provided. The laboratory sample distribution system can have a transport device and a plurality of sample container carriers. The sample container carriers can each comprise at least one magnetically active device such as, for example, at least one permanent magnet. The sample container carriers can be adapted to carry a sample container containing a sample. The magnetic actuators of the transport device units of the transport device can be suitably driven for generating a magnetic field such that a driving force can be applied to each of the sample container carriers for transporting the sample container carriers on the surface pieced together of driving surface modules of the units. The distribution system, in addition, in one embodiment, can comprise additional conveyor devices for moving a sample container carrier along a defined path.

A laboratory automation system with a plurality of pre-analytical, analytical and/or post-analytical stations and with a distribution system having a transport device and number of sample container carriers can be provided.

Referring initially to FIG. 1, FIG. 1 schematically shows a top view of a transport device 1 comprising a support frame 2 and several, in the embodiment shown, twenty actuator modules 3. The support frame 2 can comprise several support bars 21. The actuator modules 3 can be arranged in a grid pattern such as, for example, a square grid pattern. In the embodiment shown in FIG. 1, a driving surface plane of the transport device 1 can be tiled comprising several driving surface modules 4. Each driving surface module 4 can be assigned to one actuator modules 3. The actuator modules 3 can be mounted to the support frame 2. Each of the actuator modules 3 shown can have a substantially square shape allowing building of transport devices 1 of various designs by adding additional actuator modules 3 at either side of already existing modules 1 and/or removing actuator modules 3 from the device 1 shown in FIG. 1. Actuator modules having a substantially square shape with four corners can be particularly suitable for being supported by four support brackets 5 (see FIG. 3). Each support bracket 5 can be provided with one support structure 50 arranged at a node of a square grid pattern. In other embodiments, the actuator modules and/or the driving surface modules can have a substantially triangular shape or a substantially hexagonal shape.

Figure 2:
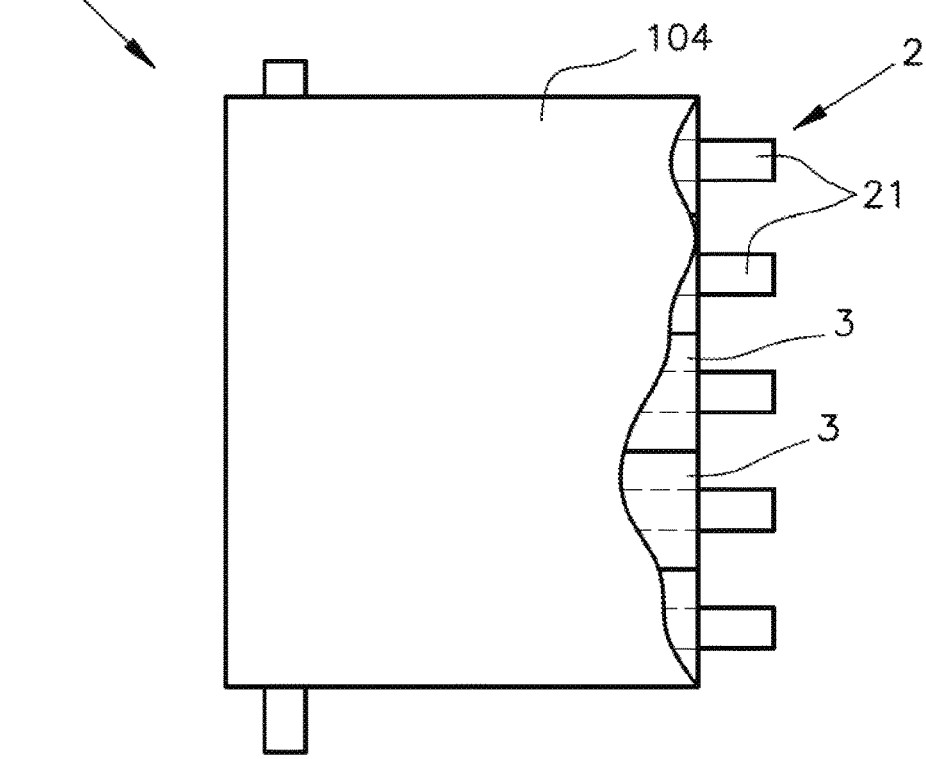
FIG. 2 illustrates a top view of a transport device comprising several actuator modules mounted to a support frame according to another embodiment of the present disclosure.

FIG. 2 schematically shows a top view of a second embodiment of a transport device 1 comprising several actuator modules 3 mounted to a support frame 2 in a grid pattern such as, for example, a square grid pattern. The support frame 2 can comprise support bars 21 to which the actuator modules 3 can be mounted. In contrast to FIG. 1, a driving surface of the transport device 10 shown in FIG. 2 is not tiled. Instead, one driving surface panel 104 can be placed on top of several actuator modules 1. In the embodiment shown in FIG. 2, the driving surface panel 104 can cover all actuator modules 3 of the transport device 10.

Figure 3:
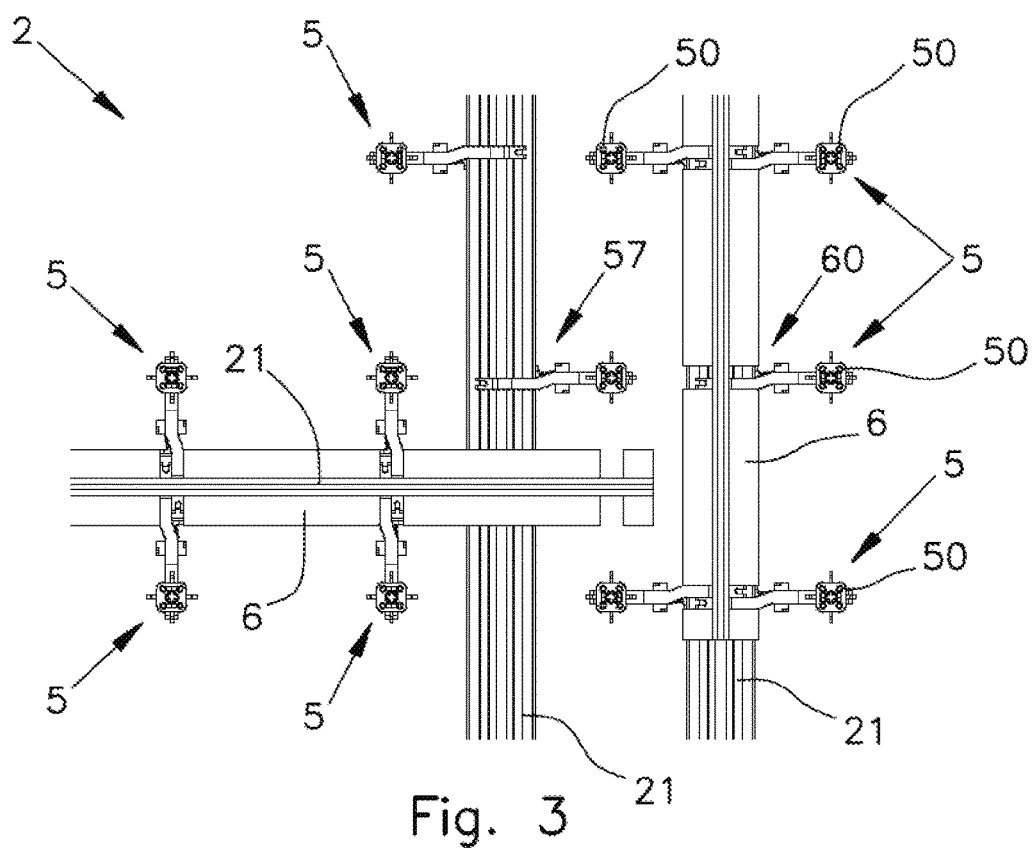
FIG. 3 illustrates a top view of a support frame and a device for mounting actuator modules of a transport device of FIG. 1 or 2 according to an embodiment of the present disclosure.
Figure 4:
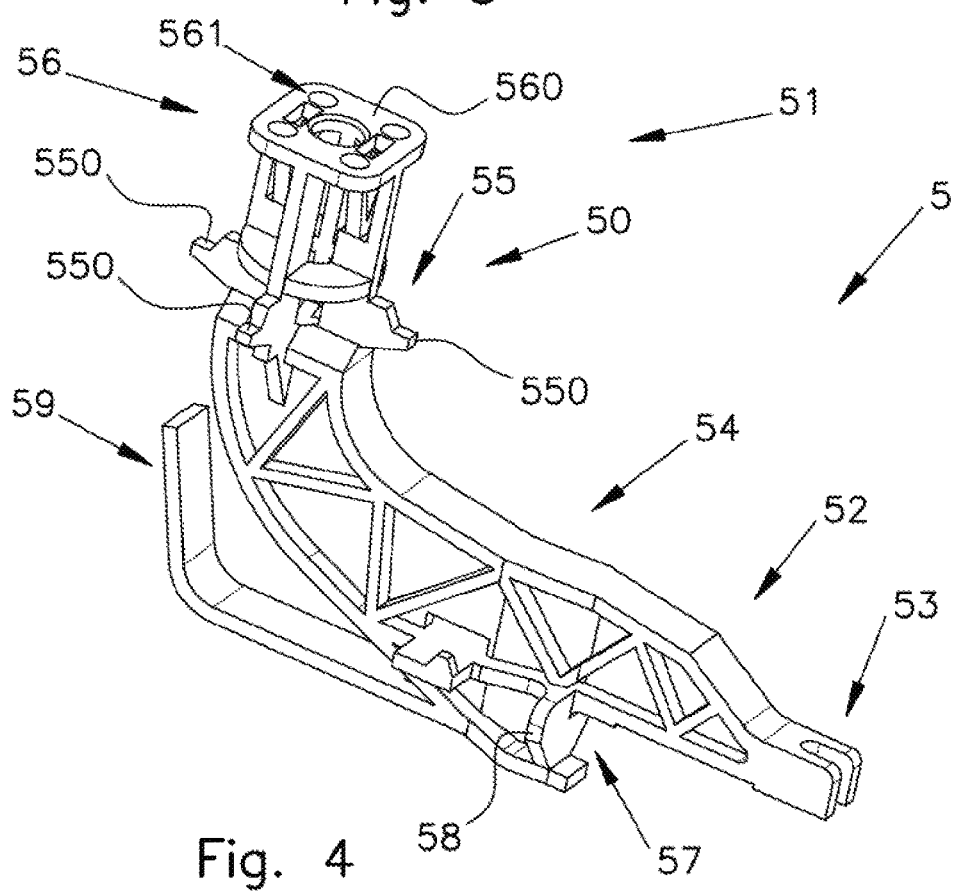
FIG. 4 illustrates a perspective view of a support bracket of the device of FIG. 3 according to an embodiment of the present disclosure.
Figure 5:
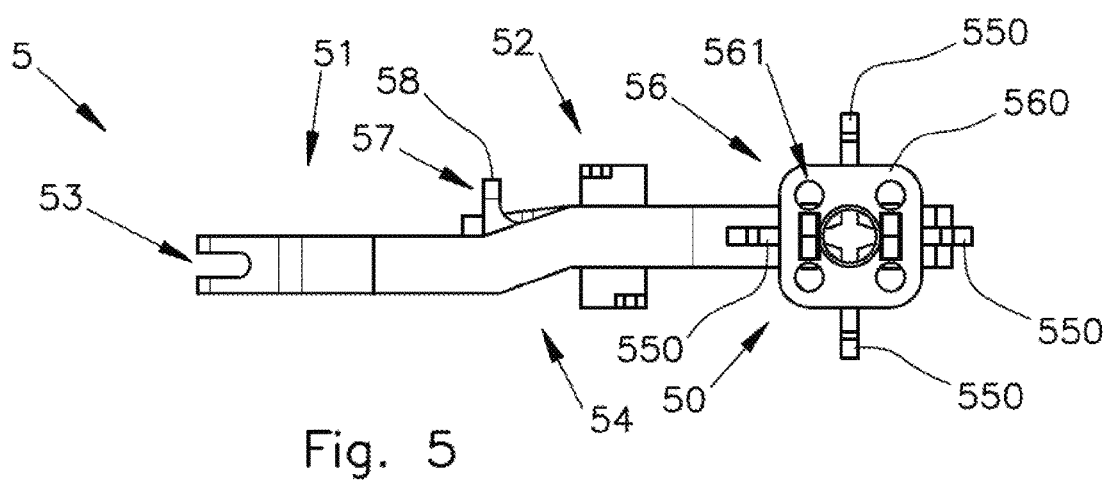
FIG. 5 illustrates a top view of the support bracket of FIG. 4 according to an embodiment of the present disclosure.

FIG. 3 is a top view of a support frame 2 with support bars 21 and a device for mounting actuator modules 3 of FIG. 1 or 2 to the support frame 2. The device can comprise several support brackets 5 with support structures 50 arranged at nodes of the grid pattern. FIGS. 4 and 5 show a support bracket 5 in a perspective view and a top view, respectively.

Each actuator modules 3 can be supported by the support structures 50 of several support brackets 5, which support structures 50 can be arranged at nodes of the grid pattern. In the embodiment shown having a square grid pattern, corners regions of up to four actuator modules 3 can be supported using one support bracket 5. The number of actuator modules 3 coupled by one support bracket 5 can depend on the basic shape of the actuator module 3, and, hence the pattern in which the actuator modules 3 can be arranged. In the case the actuator modules to be supported have a substantially triangular shape, corners regions of up to six actuator modules can be supported using one support bracket 5. In the case the actuator modules to be supported have a substantially hexagonal shape, corners regions of up to three actuator modules can be supported using one support bracket 5.

The support brackets 5 can be mounted to the support bars 21, for example, by using slot nuts (not shown). In order to simplify a positioning of each support bracket 5 along the support bars 21 and to align a plurality of support brackets 5, the device can comprise mounting rails 6.

As best seen in FIG. 4, the support bracket 5 can be essentially L-shaped seen in a side view comprising a supporting leg 51 with the support structure 50 and mounting leg 52 for mounting the support bracket 5 to one support bar 21. As shown in FIG. 3, the L-shaped support brackets 5 can be mounted to the support bars 21 such that the mounting leg 52 can protrude to a side of the support bar 21 in a direction at least substantially perpendicular to the longitudinal axis of the support bar 21. The supporting leg 51 can protrude in an at least substantially vertical direction.

At a distal end of the mounting leg 52, a slit 53 can be provided for receiving a screw or bolt (not shown) for mounting the support bracket 5 to the support bar 21 (see FIG. 3). In other embodiments, a throughhole can be provided. Providing a slit 53 instead of a throughhole can allow approaching of the support bracket 5 from a direction substantially perpendicular to the support bars 21 and substantially perpendicular to an axis of the screw or bolt. A movement of the support bracket 5 towards the support bar 21 can be limited by a stop element 57.

As best seen in FIG. 5, the mounting leg 52 can be provided with a step 54, so that the mounting leg 52 and the supporting leg 51 can be offset in an axial direction of the support bar 21. The offset can be about half the width of the support bracket 5. This can allow aligning the support structures 50 of two abutting supporting brackets 5 arranged at opposite sides of a support bar 21 in the longitudinal direction of the support bar 21.

As best seen in FIG. 3, in the embodiment shown, the mounting rail 6 can be provided with slits 60 having a width that can be twice the width of the support bracket 5. Two abutting support bracket 5 can be inserted in one slit 60 of the mounting rail 6 from opposite sides of the support bar 21 with the mounting leg 52 of each support bracket 5 abutting one side wall of the slit 60 and the two support legs 51 being arranged centered in the slit 60. Further, as shown in FIG. 3, it can also be possible to insert only one support bracket 5 in one slit 60. In case no second support bracket 5 can be inserted into one slit 60, an incorrect positioning or tilting of the support bracket 5 can be prevented by the stop element 57. For this purpose, the stop element 57 can be provided with a wing element 58 protruding from a side of the support bracket 5 over a distance equal to the width of the support bracket 5.

At the distal end of the supporting leg 51, the support structure 50 can be provided. The support structure 50 can comprise a cross element 55 with several fingers 550 adapted to support corners of actuator modules 3 at a respective node. In the embodiment shown, square actuator modules 3 arranged in a square grid pattern can be provided. Hence, the cross element 55 can have four fingers 550 arranged at angles of about 90° to each other. In the embodiment shown, each corner region of an actuator module 3 can be supported by two fingers 550, which fingers 550 in each case can extend in parallel to the two adjacent sides of neighboring actuator modules 3. Each finger 550 can be adapted to support two neighboring actuator modules 3 at their adjacent sides. In other embodiments not shown, the four fingers can each be arranged to support one corner region of one actuator module and can extend in the direction of a bisector of the corner region.

The support structure 50 can further be provided with a pillar element 56 having planar top surface 560 adapted to support a driving surface 104 spanning several actuator modules 3 (see FIG. 2) or a driving surface module 4 (see FIG. 1). At the planar top surface 560, four apertures 561 can be adapted for receiving positioning pins (41, see FIG. 7) provided at corners of the driving surface modules 4. In the case of triangular driving surface modules, the corner supports can be provided with six apertures. In the case of hexagonal driving surface modules, the corner supports can be provided with three apertures.

The support bracket 5 shown can further be provided with a cable support 59. The cable support 59 can position and support cables and/or other media supply lines (not shown) for a media supply of the actuator module 3 and/or other elements of the transport device. In the embodiment shown, the cable support 59 can be arranged below the supporting leg 51 and can extend substantially in parallel to the supporting leg 51.

Figure 6:
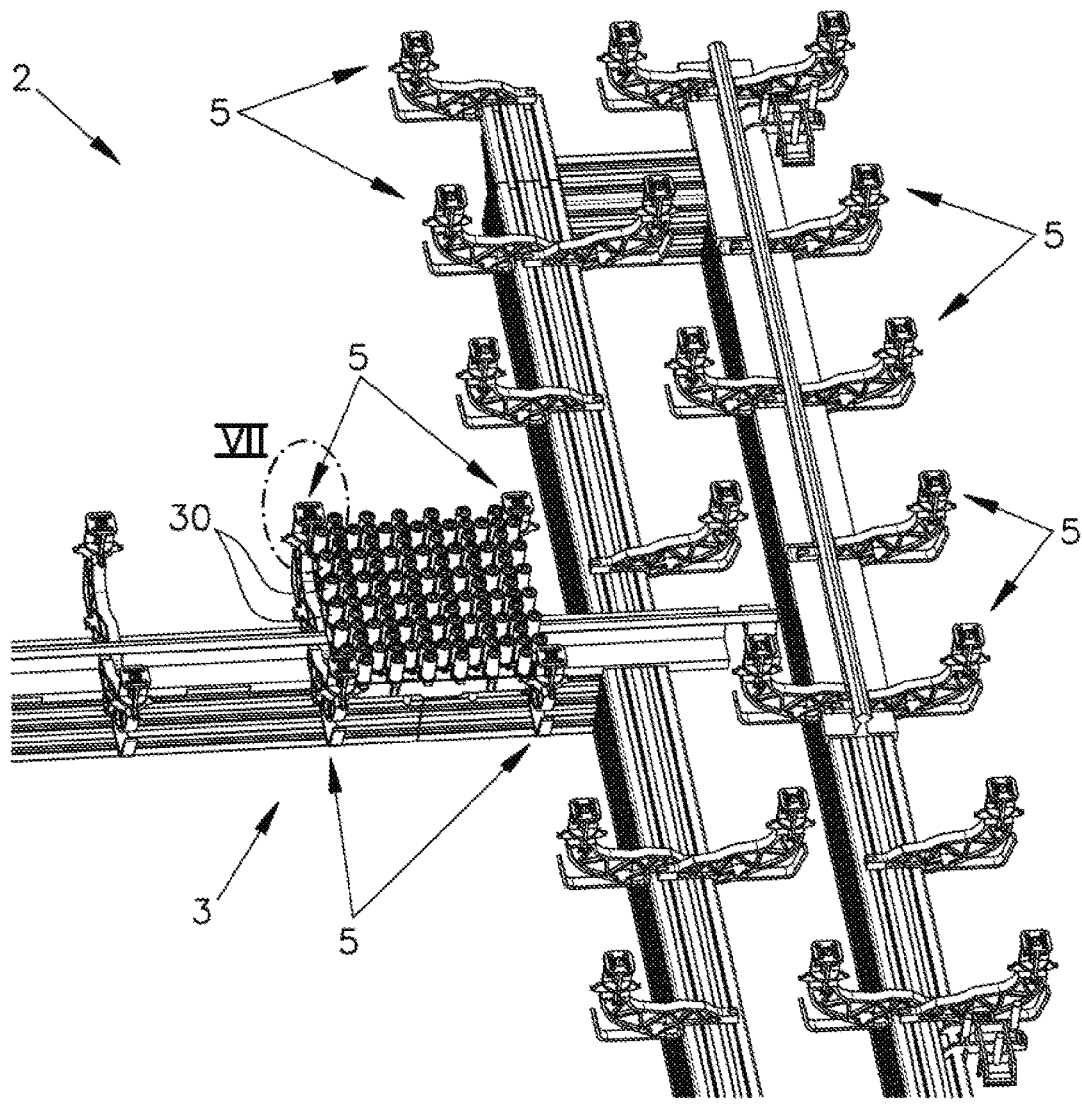
FIG. 6 illustrates a perspective view of the device of FIG. 3 and an actuator module according to an embodiment of the present disclosure.
Figure 7:
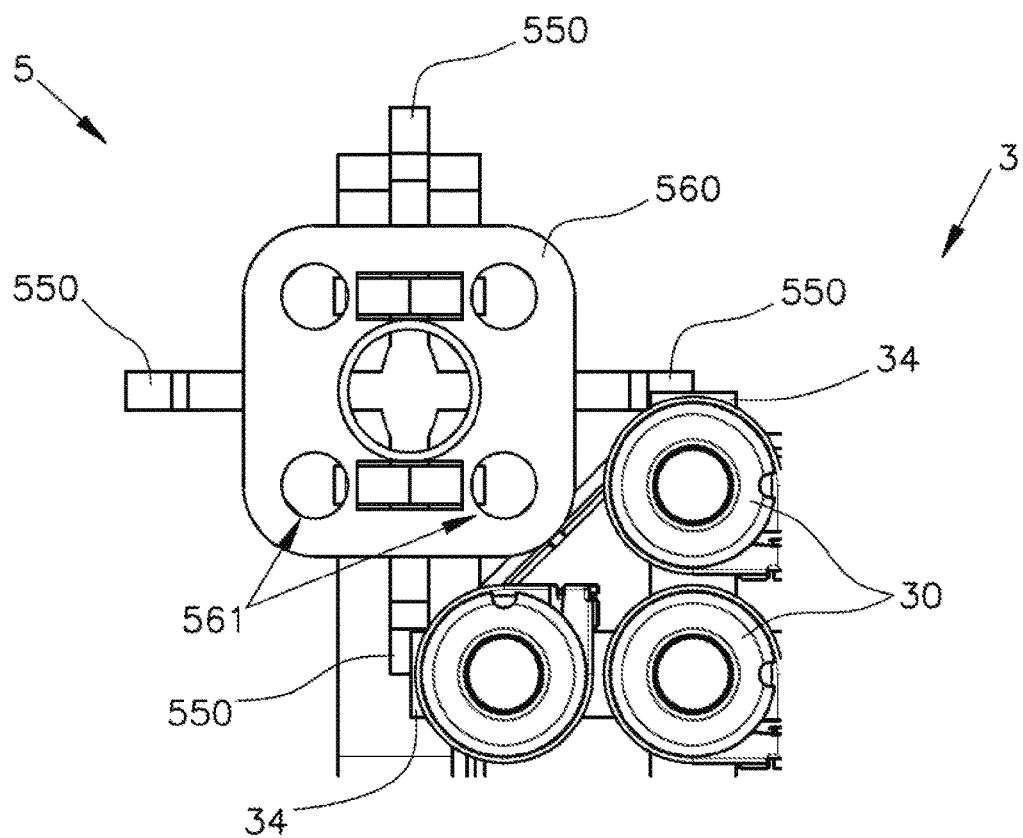
FIG. 7 illustrates a top view of a detail VII of FIG. 6 according to an embodiment of the present disclosure.

FIG. 6 shows the support structure 2 of FIG. 3. One actuator module 3 can comprise a number of electro-magnetic actuators 30 mounted to four support brackets 5. FIG. 7 shows a detail VII of FIG. 6 in a top view.

As best seen in FIG. 7, in the embodiment shown, a grid structure 34 of the actuator module 3 can rest on two fingers 550 arranged at an angle of about 90° to each other. Each finger 550 can be adapted to support an additional actuator module 3 (not shown), which can be arranged adjacent to either one of the side faces of the actuator module 3 shown. In the embodiment shown, the corner region of the actuator module 3 can be provided with a chamfer allowing the arrangement of the actuator module 3 close to the support structure 50. Further, the corner region can partly be received in a recess provided in the pillar element 56 underneath the top surface 560. The pillar element 56 can be longer than the actuators 30 so that the top surface 560 adapted for supporting a driving surface or driving surface modules 3 can be arranged above the upper end of the actuators 30.

Figure 8:
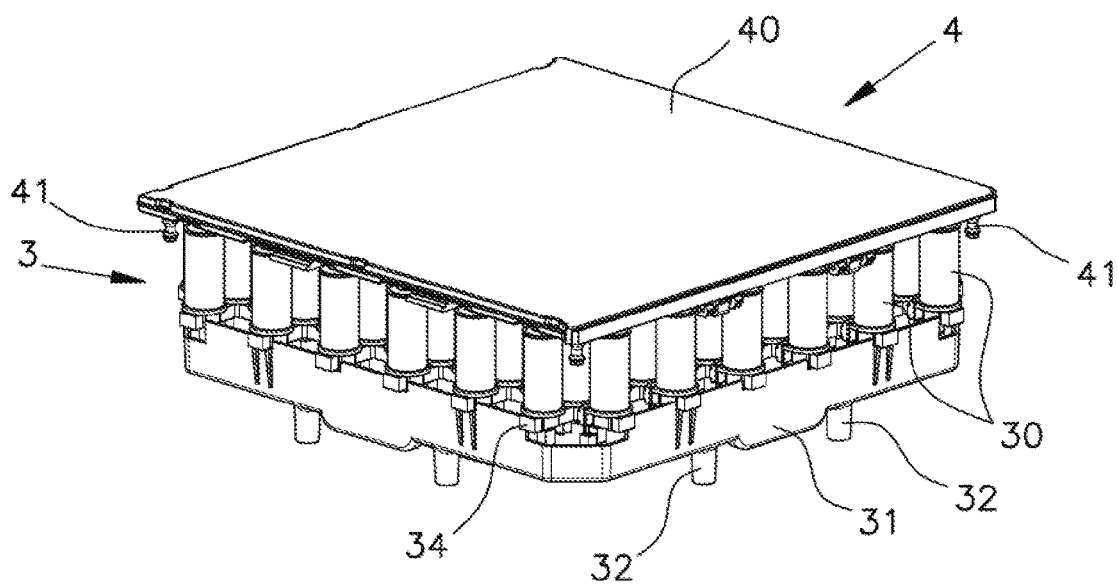
FIG. 8 illustrates a perspective view of an actuator module and a driving surface module for the transport device of FIG. 1 according to an embodiment of the present disclosure.

One actuator module 3 together with a driving surface module 4 is shown in more detail in FIG. 8. The actuator module 3 shown can have a substantially square shape with four equal sides and four corners. It can be adapted to be mounted to the support brackets 5, wherein, in the embodiment shown, the corners of the actuator module 3 can be chamfered. The corners of the driving surface module 4 may not be chamfered to provide a gapless driving surface.

The actuator module 3 can comprise a carrier element 31 with stands 32 protruding from the bottom surface. The actuator module 3 can be placed on the stands 32 for example during transport, for storage and/or for an assembly. In the embodiment shown, the actuator module 3 can comprise a grid structure 34 made of a magnetically conductive material such as, for example, a metal. The actuators 30 can be mounted to the grid structure 34. The grid structure 34 can be a rigid structure. In the embodiment shown, the grid structure 34 can be further used for supporting the actuator module 3 on the support brackets 5 (see FIG. 7).

In the embodiment shown, one driving surface module 4 can be provided on top of each actuator module 3 with a driving surface element 40 made of a material suitable for slidingly transporting sample carriers (not shown) along the top surface of the driving surface element 40. The driving surface element 40 can have a substantially square shape with four sides of equal length and four corners. The dimension of the driving surface module 4 can be at least essentially the same than that of the actuator module 3.

At the four corners of the driving surface module 4, connection pins 41 can be provided for mounting the driving surface module 4 via the support brackets 5 to the support frame 2 (see FIG. 3). The connection pins 41 can be adapted to be inserted into the apertures 561 provided at the top surface 560 of the support brackets 5. Hence, several driving surface modules 4 can be aligned by the support brackets 5.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A system, the system comprising:
a plurality of actuator modules;
a support frame with a support bar; and
a device for mounting a plurality of actuator modules in a grid pattern to the support frame, each actuator module having a regular polygonal basic shape with three, four or six corners, wherein corners of neighboring actuator modules define nodes of the grid pattern, the device comprising:
a plurality of support brackets mountable to the support bars, wherein each support bracket is provided with a support structure arranged at one of the nodes of the grid pattern and having a cross element adapted to support all corner regions of neighboring actuator modules of the node.

2. The system according to claim 1, further comprising fixation elements adapted for fixing the support brackets adjustable in position to the support bars, and
at least one mounting rail for positioning and aligning at least a subset of the support brackets on one of the support bars of the support frame.

3. The system according to claim 1, wherein at least some of the support brackets are at least essentially L-shaped in a side view comprising a supporting leg with the support structure and mounting leg for mounting the support bracket to the support frame.

4. The system according to claim 3, wherein the mounting leg is provided with a slit for an insertion of a fixation screw perpendicular to a screw axis.

5. The system according to claim 3, wherein at least some of the support brackets are provided with a step in a top view so that the mounting leg is offset to the supporting leg in a direction perpendicular to a side of the support bracket.

6. The system according to claim 5, wherein the mounting leg is offset to the supporting leg over a distance that equals half the width of the support bracket.

* * * * *